(12) United States Patent
Krejci et al.

(10) Patent No.: US 8,299,092 B2
(45) Date of Patent: Oct. 30, 2012

(54) DERIVATIVES OF 2-PHENYL-3-HYDROXYQUINOLINE-4(1H)-ONE AND METHODS OF THEIR PREPARATION AND UTILIZATION

(75) Inventors: Petr Krejci, Olomouc (CZ); Pavel Hradil, Olomouc (CZ); Jan Hlavac, Prostejov (CZ); Marian Hajduch, Olomouc (CZ)

(73) Assignee: Univerzita Palackeho (CZ)

( * ) Notice: Subject to any disclaimer, the term of this patent is extended or adjusted under 35 U.S.C. 154(b) by 532 days.

(21) Appl. No.: 12/439,723

(22) PCT Filed: Jul. 26, 2007

(86) PCT No.: PCT/CZ2007/000075
§ 371 (c)(1),
(2), (4) Date: May 6, 2009

(87) PCT Pub. No.: WO2008/028427
PCT Pub. Date: Mar. 13, 2008

(65) Prior Publication Data
US 2010/0022587 A1    Jan. 28, 2010

(30) Foreign Application Priority Data
Sep. 4, 2006 (CZ) ................. PV 2006-546

(51) Int. Cl.
*A61K 31/4709* (2006.01)
*C07D 215/00* (2006.01)
(52) U.S. Cl. ..................... 514/312; 546/155
(58) Field of Classification Search .............. None
See application file for complete search history.

(56) References Cited

FOREIGN PATENT DOCUMENTS
WO    WO 94/02145    *    2/1994
WO    WO 94/02145 A2    3/1994

OTHER PUBLICATIONS

Sui, Z. et al. Synthesis and topoisomerase inhibitory activities of novel aza-analogues of flavones. Eur. J. Med. Chem. 1999, vol. 34, p. 381.*
Dorwold, FZ. Side Reactions in Organic Synthesis. Wiley. 2005, preface.*
Hradil, P. et al. Synthesis of 2-aryl-3-hydroxyquinolin-4(1H)-ones. Collect. Czech. Commun. 1995, vol. 60, p. 1357.*
International Search Report dated Feb. 12, 2008, issued in corresponding international application No. PCT/CZ2007/000075.
T. W. M. Spence, et al., "The Chemistry of Nitro-compounds, Part I, Acid-catalysed Ring-opening Reactions of Substituted o-Nitrophenylethylene Oxides Involving Participation By the Nitro-group," J. Chem. Soc. (C), 1971, pp. 3712-3719.
Pavel Hradil, et al. "Synthesis of 2-Aryl-3-Hydroxyquinolin-4-(1H)-Ones," Collect. Czech. Chem. Commun., vol. 60, 1995, pp. 1357-1366.
Zhihua Sui, et al., "Synthesis and Topoisomerase Inhibitory Activities of Novel Aza-Analogues of Flavones," Eur. J. Med. Chem., vol. 34, 1999, pp. 381-387.
Lester A. Mitscher, "Bacterial Topoisomerase Inhibitors: Quinolone and Pyridone Antibacterial Agents," Chem. Rev., vol. 105, 2005, pp. 559-592.
P. Hradil, et al., "3-Hydroxy-2-phenyl-4(1H)-quinolinones as Promising Biologically Active Compounds," Mini-Reviews in Medicinal Chemistry, vol. 9, 2009, pp. 696-702.
V. Noskova, "In vitro chemoresistance profile and expression/function of MDR associated proteins in resistant cell lines derived from CCRF-CEM, K562, A549 and MDA MB 231 parental cells," Neoplasma, vol. 49, No. 6, 2002, pp. 418-425.
Jan Šarek, et al., "New Lupane Derived Compounds with Pro-Apoptotic Activity in Cancer Cells: Synthesis and Structure—Activity Relationships," J. Med. Chem., vol. 46, 2003, pp. 5402-5415.
Petr Džubák, et al., "New derivatives of silybin and 2, 3-dehydrosilybin and their cytotoxic and P-glycoprotein modulatory activity," Bioorganic & Medical Chemistry, vol. 14, 2006, pp. 3793-3810.
Alexandr Jegorov, et al., "Nonribosomal cyclic peptides: specific markers of fungal infections," Journal of Mass Spectrometry, vol. 41, 2006, pp. 563-576.
Soural et al., "2-Phenylsubstituted-3-Hydroxyquinolin-4(1H)-one-Carboxamides: Structure-Cytotoxic Activity Relationship Study,"*ACS Combinatorial Science*, 2011, 13, 39-44.
Soural et al., "Synthesis and cytotoxic activity of substituted 2-phenyl-3-hydroxy-4 (1H)-quinolinones-7-carboxylic acids and their phenacyl esters," *European Journal of Medicinal Chemistry*, 2006, 41, 467-474.

* cited by examiner

*Primary Examiner* — Kamal Saeed
(74) *Attorney, Agent, or Firm* — Ostrolenk Faber LLP

(57) ABSTRACT

Derivatives of 2-phenyl-3-hydroxyquinoline-4(1H)-one of the general formula (II), where X represents a nitro group, amino group, and Y represents an atom of halogen, oxygen or sulphur substituted by $C_1$ to $C_6$ alkyl or phenyl group, whereby both the alkyl and phenyl group may be further substituted and the substituents may be identical or different, or by nitrogen substituted independently by hydrogen, $C_1$ to $C_6$ alkyl, $C_1$ to $C_6$ alkyl, which may be substituted among others by halogen, hydroxy, $C_1$ to $C_4$ alkoxy or $C_1$ to $C_4$ alkylamino group, or may form a saturated or unsaturated heterocyclic ring with 5 to 7 atoms, where the individual ring atoms comprise atoms of carbon, and any of the carbon atoms may be substituted by an atom of nitrogen, sulphur or oxygen, X and Y together form an imidazo group, or imidazo group substituted by $C_1$ to $C_6$ alkyl, which may be substituted among others by halogen, hydroxy, $C_1$ to $C_4$ alkoxy or $C_1$ to $C_4$ alkylamino group, CHO or acetylgroup, or a heterocyclic ring with 5 to 6 atoms, where the ring atoms may be further substituted. Methods of preparation of these compounds are described. In addition, their cytostatic, cytotoxic, antiproliferation and immunosuppressive activity is described including examples of their potential pharmacological and pharmaceutical utilization.

(II)

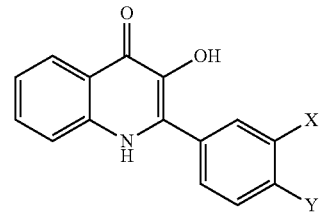

2 Claims, No Drawings

DERIVATIVES OF 2-PHENYL-3-HYDROXYQUINOLINE-4(1H)-ONE AND METHODS OF THEIR PREPARATION AND UTILIZATION

CROSS REFERENCE TO RELATED APPLICATIONS

The present application is a 35 U.S.C. §371 National Phase conversion of PCT/CZ2007/000075, filed Jul. 26, 2007, which claims benefit of Czech Application No. PV 2006-546, filed Sep. 4, 2006. The PCT International Application was published in the English language.

TECHNICAL FIELD

The invention describes derivatives of 2-phenyl-3-hydroxyquinoline-4(1H)-one, which show biological activity.

BACKGROUND ART

So far, derivatives of 2-phenyl-3-hydroxyquinoline-4(1H)-one referred to in the present invention have not been described in literature. Derivatives of 2-phenyl-3-hydroxyquinoline-4(1H)-one of the general formula I have been described in the literature

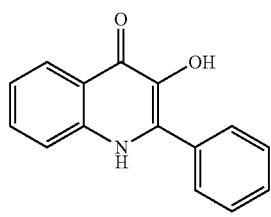

(I)

as well as some other of its derivatives, which are substituted by various substituents.

A derivative substituted by chlorine atom in the position 6 of the quinolone skeleton has been described in the paper by Spence et al. (J. Chem. Soc., 1971, 3712-3719.). Preparation of this derivative is further described, which is based on o-nitrobenzaldehyde (1), which upon reaction with bromacetonphenon using the Darzens reaction yields trans-1-benzoyl-2-(o-nitrophenyl)ethylene epoxide (2), which under the activity of hydrogen chloride gives rise to 6-chlorine-1,3-dihydroxy-2-phenylquinoline-4(1H)-one (3), which upon subsequent reduction by dithionite yields 6-chlorine-2-phenyl-3-hydroxyquinoline-4(1H)-one (4), as shown in the Scheme 1.

Scheme 1

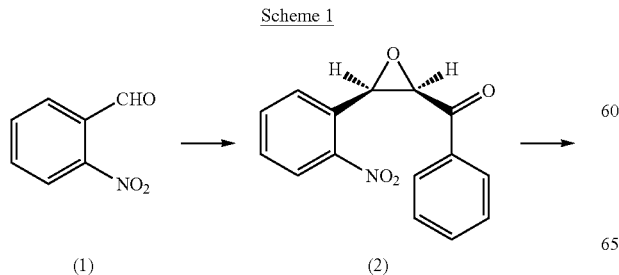

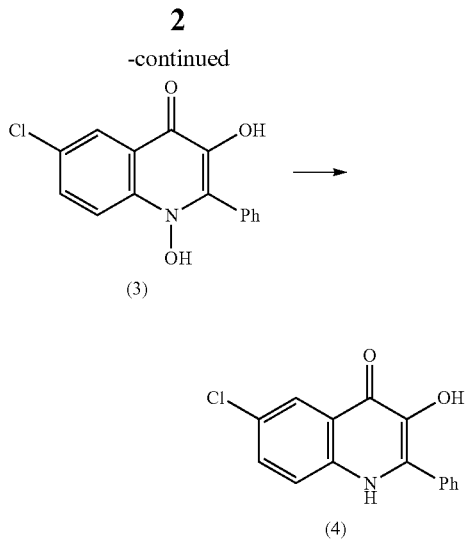

Sui et al. (Eur. J. Med. Chem., 1999, 34, 381.) described preparation of substituted derivatives containing hydroxy group in the position 5 and 7 and a combination of substituents of e.g. hydrogen atom, halogen atom or trifluormethyl group or hydroxy group in the position 3', 4' and 5'. These derivatives are inhibitors of procaryotic topoisomerase II and DNA gyrase. Preparation of these derivatives is based on substituted aniline (5), which yields a ketone (6) by Susagawa's acylation with suitable acetonitrile. Ring closure to 3-methoxy-4quinolones (7) is achieved upon subsequent N-acylation by benzoylchloride and under subsequent activity of sodium methanolate. Derivatives of quinolone (8) shown in the Scheme 2 are produced upon subsequent demethylation by hydrogen bromide.

Scheme 2

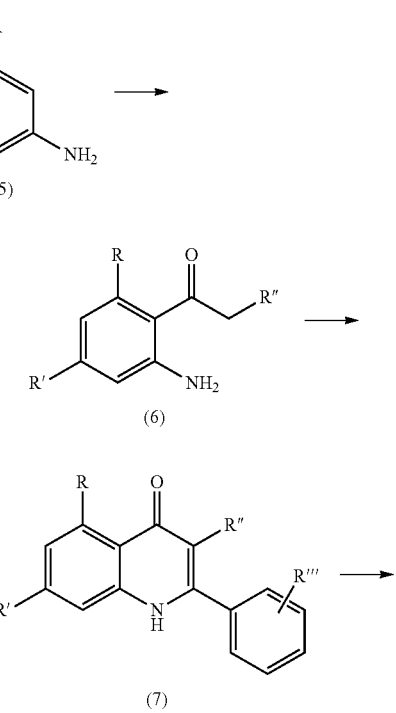

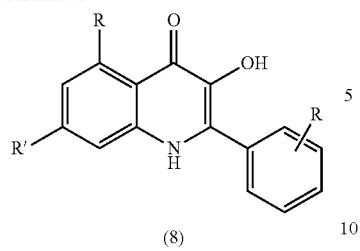

(8)

R, R″, R‴ = H, OH, OMe, F, Cl, Br, CF₃

Hradil et al. (Collect. Czech. Chem. Commun., 1995, 60, 1357) described preparation of derivatives containing combinations of substituents such as hydrogen atoms, halogen atoms, nitro- or amino groups or amino groups substituted by isopropyl in the position 2', 3', 4' and 5'. Preparation of these derivatives is based on a suitable substituted salt of anthranilic acid (9), which upon reaction with bromacetonphenon yields phenacyl esters (10), which yield quinolone derivatives (11) upon ring closure with polyphosphoric acid—(Scheme 3).

Scheme 3

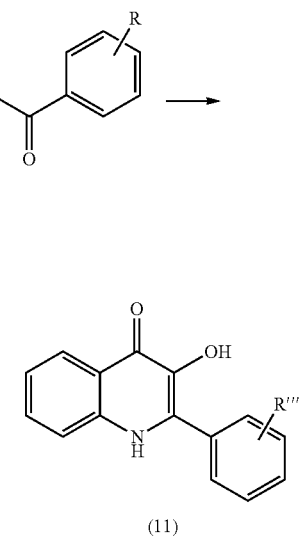

R = H, Cl, Br, NO₂, NH₂, NH'Pr

DISCLOSURE OF INVENTION

The invention discloses derivatives of 2-phenyl-3-hydroxyquinoline-4(1H)-one of the general formula (II),

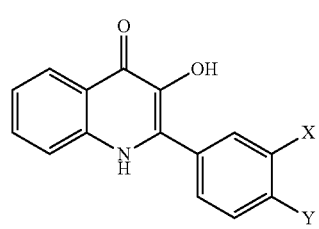

where

X is a nitro group or a amino group, and

Y is a halogen, oxygen or sulphur atom substituted by carbon chain $C_1$ to $C_6$ with simple or multiple bonds or a phenyl group where both the alkyl and the phenol group may be further substituted and the substituents may be identical or different and may consist of a halogen, hydroxy, alkyl with 1 to 4 carbons, or an alkoxy group with 1 to 4 carbon atoms, or an alkylamino group with 1 to 4 carbon atoms, or a nitrogen atom substituted independently by hydrogen, carbon chain $C_1$ to $C_6$ with simple or multiple bonds, whereby the individual atoms of the chain may be further substituted among others by halogen, hydroxy, alkoxy group with carbon number 1 to 4, or alkyl amino group with carbon number 1 to 4, or may constitute a saturated or unsaturated heterocyclic ring with 5 to 7 atoms, where the individual ring atoms comprise carbon atoms, of which any can be replaced by a nitrogen, sulphur or oxygen atom, and the nitrogen atoms may be further bound to a nitrogen atom X through a methine group.

The invention discloses also include the derivative of the general formula III

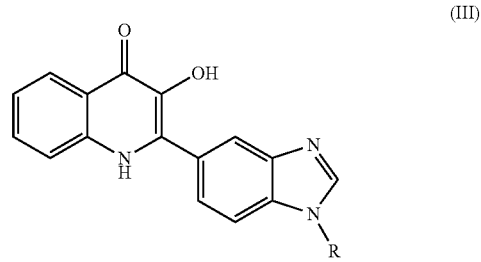

where R indicates a hydrogen or a carbon chain $C_1$ to $C_6$ with simple or multiple bonds, which may be substituted among others by halogen, hydroxy, $C_1$ to $C_4$ alkoxy or $C_1$ to $C_4$ alkylamino group, formyl or acetyl group, or saturated or unsaturated heterocyclic ring with 5 to 6 atoms, where the ring atoms may be further substituted.

The invention discloses also include the method of preparation of the derivatives of 2-phenyl-3-hydroxyquinoline-4 (1H)-one of the general formula (II), whereby the compounds of the general formula (II), where X is a nitro group and Y is a halogen, are prepared by ring closure of 2-(4-halogen-3-nitrophenyl)-2-oxoethyl 2-aminobenzoate in acids such as polyphosphoric acid, trifluoracetic acid or formic acid, or in solvents with high boiling point such as N-methylpyrrolidone or N-cyclohexylpyrrolidone at temperatures from 50 to 200° C., usually at 100° C. temperature (Scheme 4);

Scheme 4

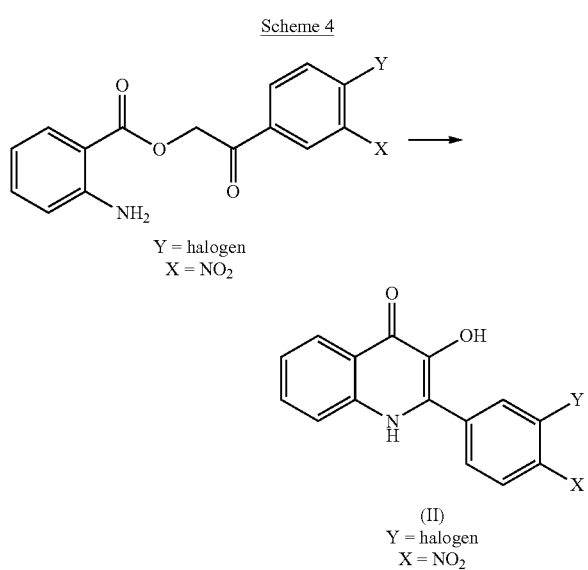

The invention discloses also include the Method of preparation of the derivatives of 2-phenyl-3-hydroxyquinoline-4 (1H)-one of the general formula (II), where X is a nitro group and Y is a variably substituted nitrogen atom, which are prepared by reaction of a suitably substituted amino compound with a compound of the general formula (II), where X is a nitro group and Y is a halogen in surplus of the reacting amino compound or in the mixture of the amino compound with N-methyl-pyrrolidone at 70 to 150° C. temperature, usually at the boiling point of the reacting mixture (Scheme 5);

Scheme 5

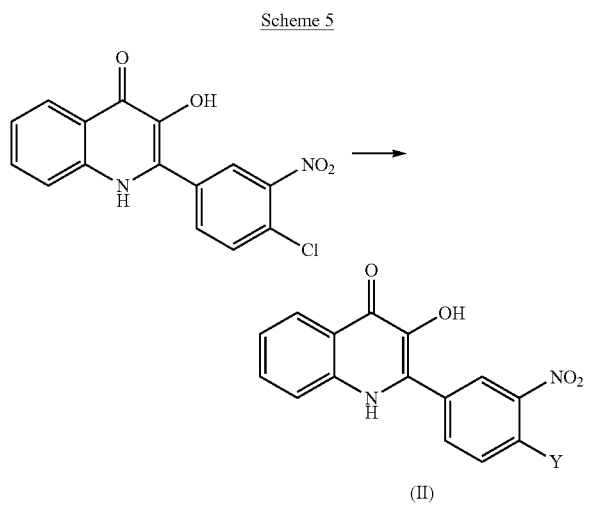

The invention discloses further include the method of preparation of the derivatives of 2-phenyl-3-hydroxyquinoline-4(1H)-one of the general formula (II), where X is a nitro group and Y is a nitrogen atom comprising a part of unsaturated heterocycle, or a substituted sulphur or oxygen atom, which are prepared by reaction of a suitably substituted heterocycle or thiocompound with a compound of the general formula (II), where X is a nitro group and Y is a halogen in N-methyl-pyrrolidone or an alcohol with higher boiling point at the presence of strong bases such as sodium hydride or sodium alcoholate, at 70 to 220° C. temperature, usually at the boiling point of the reacting mixture (Scheme 5);

Finally, the invention discloses include the method of preparation of the derivatives of 2-phenyl-3-hydroxyquinoline-4 (1H)-one of the general formula (III). Compounds of the general formula (III) are prepared from a compound of the general formula (II), where X is a nitro group and Y is a nitrogen atom substituted by a hydrogen atom and another substituent according to the description given in the first paragraph of the chapter "Disclosure of Invention", by action of hydrogen in organic acids such as formic acid or acetic acid, at the presence of catalysts of hydrogenation, such as the Raney nickel, platinum or palladium on activated carbon, where first the nitro group is reduced and then followed by ring closure to the corresponding compound of the general formula (III) at the temperature 0 to 150° C. temperature, usually at the boiling point of the reacting mixture (Scheme 6)

Scheme 6

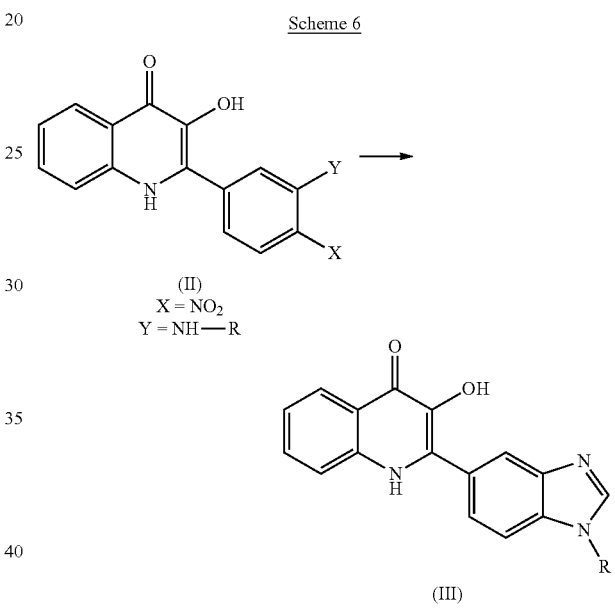

The invention discloses also include the method of use of the derivatives according to the requirements 1 and 2 for treatment of tumorous diseases, diseases with pathological proliferation and diseases featuring pathological activation of the immunity system, for example the autoimmune and hypersensitivity diseases

EXAMPLES

The essence of the methods according to the invention is further demonstrated in the following examples. These examples have an illustrative character and do not limit the extend of the invention in any case.

Example 1

2-(4-Chlorine-3-nitrophenyl)-3-hydroxyquinoline-4 (1H)-one 2-(4-Chlorine-3-nitrophenyl)-2-oxoethyl 2-aminobenzoate (44.8 mmol) was suspended in polyphosphoric acid (167.3 g). The reaction mixture was heated to 100° C. and stirred for ninety minutes at this temperature. The mixture was then poured into water with crushed ice (700 ml). The separated product was filtered off, washed with water into neutral reaction of filtrate and dried.

Yield: 84% by theory, melting point 284 to 287° C.: MS: m/z 319.9 [M($^{35}$Cl)+H]$^+$.

Example 2

3-Hydroxy-2-[(3-nitro-4-piperidine-1-yl)phenyl]quinoline-4(1H)-one 2-(4-Chlorine-3-nitrophenyl)-3-hydroxyquinoline-4(1H)-one (0.63 mmol) was dissolved in mixture of piperidine (6.3 mmol) and N-methylpyrrolidone (1 ml). The mixture was stirred at 110° C. temperature for two hours. The mixture was then cooled down to 20° C., water was added (20 ml) and pH was adjusted to pH 7 by diluted HCl (1:3). The separated solid was filtered off, washed with water and dried. The product was crystallized from 2-methoxyethanol.

Yield: 95% by theory, melting point 264 to 267° C., MS: m/z 365.9 [M+H]$^+$.

Example 3

3-Hydroxy-2-{4-[(3-hydroxypropyl)amino]-3-nitrophenyl}quinoline-4(1H)-one

The final product was obtained using the same procedure as in the example 2, using 3-amino-1-propanol in N-methylpyrrolidone.

Yield: 65% by theory, melting point 233 to 236° C., MS: m/z 355.9 [M+H]$^+$.

Example 4

3-Hydroxy-2-{4-[4-(2-hydroxyethyl)piperazine-1-yl]-3-nitrophenyl}quinoline-4(1H)-one The final product was obtained using the same procedure as in example 2, using N-(2-hydroxyethyl)-piperazine in N-methylpyrrolidone.

Yield: 76% by theory, melting point 218-221° C., MS: m/z 410.9 [M+H]$^+$.

Example 5

3-Hydroxy-2-(4-{4-[2-(2-hydroxyethoxy)ethyl]piperazine-1-yl}-3-nitrophenyl)quinoline-4(1H)-one The final product was obtained using the same procedure as in example 2, using 1-[2-(hydroxyethoxy)-ethyl]piperazine in N-methylpyrrolidone.

Yield: 91% by theory, melting point 203 to 204° C., MS: m/z 454.9 [M+H]$^+$.

Example 6

2-[4-(Ethylamino)-3-nitrophenyl]-3-hydroxyquinoline-4(1H)-one

The final product was obtained using the same procedure as in example 2, using ethylamine in N-methyl pyrrolidone.

Yield: 95% by theory, melting point 282 to 285° C., MS: m/z 326.0 [M+H]$^+$.

Example 7

3-Hydroxy-2-[3-nitro-4-(phenylthio)phenyl]quinoline-4(1H)-one

Thiophenol (1.95 mmol) was dissolved in butanol (8.0 ml), and sodium hydride (1.95 mmol) was added to the resulting solution. After five minutes of stirring, 2-(4-chlorine-3-nitrophenyl)-3-hydroxyquinoline-4(1H)-one (1.94 mmol) was added into the reaction mixture and the mixture was refluxed for six hours.

The reaction mixture was then cooled down to 20° C. and acidified to pH 6 by diluted acid HCl (1:3). The separated product was filtered off, washed three times with ethanol and dried. It was recrystallized from 2-methoxyethanol.

Yield: 94% by theory, melting point 322 to 324° C., MS: 390.9 [M+H]$^+$.

Example 8

3-Hydroxy-2-[4-(1H-imidazole-1-yl)-3-nitrophenyl]quinoline-4(1H)-one

Imidazole (0.48 mmol) was dissolved in N-methylpyrrolidone (1.0 ml). Sodium hydride (0.48 mmol) was added to the solution, and after five minutes also 2-(4-chlorine-3-nitrophenyl)-3-hydroxyquinoline-4(1H)-one (0.4 mmol). The reaction mixture was stirred for two hours at the boiling point. It was then poured onto crushed ice and pH adjusted to pH 7 by diluted HCl (1:3). The separated product was filtered off, washed twice with water and dried up. It was recrystallized from 2-methoxyethanol.

Yield: 92% by theory, melting point 278 to 280° C., MS: m/z 349.0 [M+H]$^+$.

Example 9

3-[5-(3-Hydroxy-4-oxo-1,4-dihydroquinoline-2-yl)-1H-benzimidazole-1-yl]propyl ester of formic acid 3-Hydroxy-2-{4-[(3-hydroxypropyl)amino]-3-nitrophenyl}quinoline-4(1)-one (4.5 mmol) was suspended in formic acid (27 ml), and catalyzed 5% Pd/C (0.1 g) was added into the reaction mixture. The apparatus was blown by nitrogen, and hydrogen was then forced into the reaction mixture. The mixture was heated to boiling under reflux for six hours time. After cooling the catalyst was filtered off and the mixture was thickened on a vacuum evaporator to form viscous oil. The oil was dissolved in added water. The mixture was then neutralized to pH 7 by NaHCO$_3$ solution. The separated solid was filtered off, washed with water and dried. It was recrystallized from mixture of N-methylpyrrolidone-ethylacetate.

Yield: 95%, melting point 215 to 217° C., MS: m/z 364.0 [M+H]$^+$.

Example 10

In Vitro Antitumour Activity

In order to evaluate antitumour activity of the new prepared substances in vitro, we used the MTT cytotoxic test on cell lines derived from normal tissues and tumours. In particular, they included the NIH 3T3 (mouse fibroblasts), K562 (human myeloid leukaemia), K562-tax (human myeloid leukaemia resistant to taxol and the overexpressing protein of the PgP multiple drug resistance), CEM (T-lymphoblastic leukaemia), CEM-DNR-bulk (T-lymphoblastic leukaemia resistant to doxorubicine, lacking the expression of target gene for inhibitors of topoisomerase II alpha) and the line A549 (human lung adenocarcinoma). The expression characteristics, profiles of sensitivity to classic antitumour drugs and the methodology of the cytotoxic MTT test have been repeatedly published (Nosková V. et al., Neoplasma 2002, Šarek J. et al., Med. Chem., 2003, Džubák P., et al., Bioorg Med. Chem., 2006).

Results from the tests are summarized in Table 1. The tested substances showed generally higher cytotoxicity to tumour cells than to non-tumour ones (NIH 3T3 fibroblasts).

TABLE 1

In vitro antitumour activity of the tested substances.

| Substance of formula | Y substitution X = $NO_2$ | Cytotoxic and antiproliferation activity MTT test (IC50, μM) | | | | | | | | | |
|---|---|---|---|---|---|---|---|---|---|---|---|
| | | CEM | | CEM-DNR-BULK | | K 562 | | K562-TAX | | A 549 | |
| | | x | SD | x | SD | x | SD | x | SD | x | SD |
| II | Cl | 2.6 | 0.10 | 3.5 | 0.52 | 2.3 | 0.36 | 3.2 | 0.41 | 4.2 | 2.01 |
| II | pyrrolidinyl | 1.4 | 0.77 | 3.4 | 0.45 | 0.7 | 0.02 | 2.1 | 0.62 | 1.7 | 1.22 |
| II | piperidinyl | 1.6 | 1.02 | 3.0 | 0.29 | 0.7 | 0.03 | 2.0 | 0.73 | 1.6 | 1.03 |
| II | morpholinyl | 3.1 | 0.66 | 10.5 | 0.72 | 3.1 | 0.36 | 3.3 | 0.17 | 2.8 | 0.18 |
| II | piperazinyl-$CH_2CH_2OCH_2CH_2OH$ | 4.3 | 2.09 | 85.0 | 20.11 | 10.9 | 0.83 | 41.4 | 3.77 | 31.0 | 16.53 |
| II | —NH($CH_2)_2$OH | 2.7 | 0.15 | 98.8 | 53.82 | 7.3 | 4.05 | 44.9 | 4.55 | 46.8 | 8.89 |
| II | —NH($CH_2)_3$OH | 1.4 | 0.77 | 46.3 | 4.27 | 6.2 | 3.83 | 12.9 | 0.93 | 12.4 | 0.76 |
| II | —NH($CH_2)_4$OH | 0.7 | 0.04 | 15.1 | 1.15 | 1.8 | 1.33 | 8.6 | 1.90 | 5.7 | 4.48 |
| II | —NH($CH_2)_5$OH | 1.0 | 0.50 | 10.8 | 0.75 | 2.8 | 1.88 | 5.7 | 3.96 | 5.3 | 3.95 |
| II | —N($CH_2CH_2OH)_2$ | 0.3 | 0.02 | 142.9 | 22.05 | 186.6 | 53.46 | 198.0 | 28.22 | 224.5 | 31.35 |
| II | —N($CH_2CH_2CH_3)_2$ | 0.7 | 0.06 | 2.2 | 0.27 | 0.6 | 0.08 | 1.2 | 0.63 | 1.1 | 0.56 |
| II | —NHCH($CH_3)_2$ | 1.6 | 0.64 | 6.8 | 2.89 | 2.1 | 2.56 | 3.0 | 0.49 | 2.8 | 0.10 |
| II | —N($CH_3$)($CH_2CH_3$) | 1.7 | 0.98 | 129.1 | 16.08 | 0.7 | 0.03 | 162.7 | 16.37 | 66.5 | 57.81 |
| II | —NH(CH$_2$)$_3$Ph | 6.5 | 0.78 | 2.5 | 0.4 | 0.6 | 0.1 | 0.93 | 0.67 | 7.2 | 3.1 |
| II | —S-CH$_2$-CH=CH-CH$_3$ | 2.1 | 0.34 | 3.2 | 0.24 | 9.3 | 0.13 | 5.2 | 0.75 | 4.3 | 2.1 |
| II | X = $NH_2$ | | | | | | | | | | |
| II | —S-(4-OCH$_3$-C$_6$H$_4$) | 4.5 | 0.56 | 16.3 | 4.8 | 170 | 24.6 | 4.2 | 0.60 | 7.9 | 4.12 |
| II | —O-CH$_2$CH$_2$-O-CH$_3$ | 0.45 | 0.1 | 7.3 | 2.1 | 67 | 13.2 | 6.9 | 2.34 | 123.2 | 37.1 |
| | R substitution | | | | | | | | | | |
| III | —($CH_2)_5CH_3$ | 2.8 | 0.81 | 54 | 21.2 | 8.5 | 1.01 | 35 | 12.50 | 44.3 | 12.5 |
| III | —($CH_2)_2S(CH_2)_2OH$ | 0.8 | 0.10 | 2.2 | 0.35 | 3.1 | 0.25 | 4.5 | 0.76 | 3.6 | 0.51 |
| III | —($CH_2)_2N(C_2H_5)_2$ | 5.2 | 2.67 | 71.2 | 12.56 | 2.1 | 1.24 | 6.5 | 2.45 | 3.5 | 1.23 |

TABLE 1-continued

In vitro antitumour activity of the tested substances.

| Substance of formula | Y substitution X = NO₂ | Cytotoxic and antiproliferation activity MTT test (IC50, µM) | | | | | | | | |
|---|---|---|---|---|---|---|---|---|---|---|
| | | CEM | | CEM-DNR-BULK | | K 562 | | K562-TAX | | A 549 |
| | | x | SD | x | SD | x | SD | x | SD | x | SD |
| III | butyl-NH—(pyrimidine with 2-OH, 6-OH) | 1.0 | 0.23 | 12.43 | 4.32 | 4.3 | 1.56 | 123.1 | 28.1 | 2.1 | 0.67 |

Example 11

In Vitro Immunosuppressive Activity

The proliferation response of isolated lymphocytes to polyclonal mitogens belongs to the most important parameters of specific cell immunity. Most of the human lymphocytes occur in quiet state. Antigens or polyclonal mitogens, however, are capable of activating lymphatic cells, which is accompanied by dramatic changes of their cell metabolism (enhanced mitochondrial activity, protein and nucleic acid synthesis, formation of blastic cells and proliferations). Substances having the capability to suppress such processes show immunosuppressive activity in clinical conditions and, therefore, these tests can be used for screening tests of immunosuppressive activity in vitro. On this account, we use the above-mentioned MTT test, which evaluates both the survival and the proliferation activity of quiet vs. polyclonal-mitogen (concavaline A, 5 µg/ml)-stimulated human lymphocytes to screen the immunosuppressive activity of new substances (Jegorov et al., J. Mass. Spetrom., 2006).

Results from the tests are summarized in Table 2. Selected substances showed preferential inhibition activity to the stimulated vs. quiet lymphocytes, which is conformable with the expected immunosuppressive activity of substances.

TABLE 2

Immunosuppressive activity of the new substances.

| Substance of formula | Substitution | Inhibition of lymphocyte activation with ConA (IC50, µM) | |
|---|---|---|---|
| | | x | SD |
| II | F | 3.8 | 0.33 |
| II | pyrrolidinyl | 1.5 | 0.17 |
| II | morpholinyl | 6.3 | 0.54 |
| II | piperidinyl | 2.7 | 0.22 |
| II | 4-(2-(2-hydroxyethoxy)ethyl)piperazinyl | 5.8 | 0.62 |

TABLE 2-continued

Immunosuppressive activity of the new substances.

| Substance of formula | Substitution | Inhibition of lymphocyte activation with ConA (IC50, μM) | |
|---|---|---|---|
| | | x | SD |
| II | —NH(CH$_2$)$_2$OH | 3.8 | 0.51 |
| II | —NH(CH$_2$)$_3$OH | 0.8 | 0.09 |
| II | —NH(CH$_2$)$_4$OH | 1.1 | 0.09 |
| II | —NH(CH$_2$)$_5$OH | 0.6 | 0.08 |
| II | —N(CH$_2$CH$_2$OH)$_2$ | 0.9 | 0.11 |
| II | —N(CH$_2$CH$_2$CH$_3$)$_2$ | 0.9 | 0.13 |
| II | —NHCH(CH$_3$)$_2$ | 4.8 | 0.42 |
| II | —N(CH$_3$)(CH$_2$CH$_3$) | 5.7 | 0.55 |
| II | (methoxyethoxymethyl-3-methyl-4-propylpiperidine structure) | 0.5 | 0.1 |
| III | —CH$_2$CH$_2$NHCHO | 1.1 | 0.45 |
| III | (1-propyl-3-methyl-4-(2-hydroxyethyl)piperazine structure) | 0.8 | 0.12 |
| III | (1-butylimidazole structure) | 1.25 | 0.01 |
| III | (1-(pentan-3-yl)-1,2,3-triazole structure) | 4.6 | 1.3 |
| III | (CH$_2$CH$_2$CF$_3$ structure) | 4.2 | 1.1 |
| III | (methoxyethoxymethyl-3-methyl-4-propylpiperidine structure) | 3.7 | 1.25 |

INDUSTRIAL APPLICABILITY

Derivatives of the general formula (II) and (III) according to the invention show a wide spectrum of biological activities, for example the cytostatic, antiproliferation and immunosuppressive activity, and they are suitable for production of pharmaceutical and diagnostic applications or can be used as intermediate products in production of other derivatives of the same group.

What is claimed is:

1. Derivatives of 2-phenyl-3-hydroxyquinoline-4(1H)-one of the general formula (II),

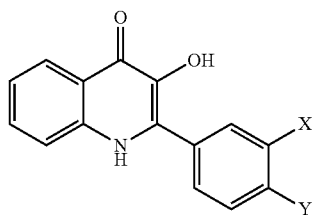

(II)

where

X represents a nitro group and

Y represents an oxygen atom substituted by a $C_1$ to $C_6$ carbon chain where the alkyl may be substituted with a halogen, hydroxy, or an alkoxy group with from 1-4 carbon atoms; an oxygen atom substituted with a phenyl group, where the phenyl may be substituted with a halogen, hydrogen or alkoxy group with from 1-4 carbon atoms; a sulfur atom substituted with a $C_1$ to $C_6$ carbon chain where the alkyl may be substituted with a halogen, hydroxy, or an alkoxy group with from 1-4 carbon atoms; a sulfur atom substituted with a phenyl group where the phenyl may be substituted with a halogen, a hydroxy or an alkoxy group with from 1-4 carbon atoms; a nitrogen atom substituted with hydrogen; a nitrogen atom substituted with a hydrogen and a $C_1$ to $C_6$ carbon chain where the alkyl may be substituted with a halogen, hydroxy, or an alkoxy group with from 1-4 carbon atoms; a nitrogen atom substituted independently with a $C_1$ to $C_6$ carbon chain where the alkyl may be substituted with a halogen, hydroxy, or an alkoxy group with from 1-4 carbon atoms and a $C_1$ to $C_6$ carbon chain where the alkyl may be substituted with a halogen, hydroxy, or an alkoxy group with from 1-4 carbon atoms; and a saturated or unsaturated 5 to 7 membered ring where 1 or 2 atoms are independently a nitrogen or oxygen atom.

2. Derivatives of 2-phenyl-3-hydroxyquinoline-4(1H)-one according to claim 1, of the general formula (III)

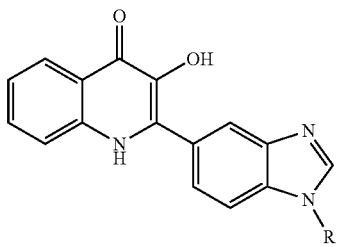

(III)

where R represents hydrogen or carbon chain $C_1$ to $C_6$ with single or multiple bonds, which can be substituted by a halogen, hydroxy, $C_1$ to $C_4$ alkoxy group, formyl or acetyl group, or saturated or unsaturated 5 to 6 membered ring where 1 or 2 atoms are independently a nigrogen or oxygen atom.

* * * * *